(12) United States Patent
Winn et al.

(10) Patent No.: US 9,138,925 B2
(45) Date of Patent: Sep. 22, 2015

(54) METHOD FOR FORMING BILAYER PATCHES

(71) Applicant: Applied Silicone Corporation, Santa Paula, CA (US)

(72) Inventors: R. Alastair Winn, Santa Barbara, CA (US); Nolan Pasko, Encinitas, CA (US)

(73) Assignee: Applied Silicone Corporation, Santa Ana, CA (US)

( * ) Notice: Subject to any disclaimer, the term of this patent is extended or adjusted under 35 U.S.C. 154(b) by 0 days.

(21) Appl. No.: 14/261,255

(22) Filed: Apr. 24, 2014

(65) Prior Publication Data

US 2014/0234636 A1 Aug. 21, 2014

Related U.S. Application Data

(62) Division of application No. 13/290,929, filed on Nov. 7, 2011, now abandoned.

(51) Int. Cl.
| | | |
|---|---|---|
| *B29C 45/16* | (2006.01) | |
| *A61F 2/12* | (2006.01) | |
| *B32B 25/20* | (2006.01) | |
| *B29C 33/56* | (2006.01) | |
| *B29C 45/00* | (2006.01) | |
| *B32B 25/08* | (2006.01) | |
| *B32B 27/28* | (2006.01) | |

(52) U.S. Cl.
CPC ............... *B29C 45/1657* (2013.01); *A61F 2/12* (2013.01); *B29C 33/56* (2013.01); *B29C 45/0001* (2013.01); *B29C 45/0055* (2013.01); *B29C 45/1615* (2013.01); *B32B 25/08* (2013.01); *B32B 25/20* (2013.01); *B32B 27/283* (2013.01); *B32B 2250/02* (2013.01); *B32B 2250/24* (2013.01); *B32B 2305/72* (2013.01); *B32B 2305/77* (2013.01); *B32B 2535/00* (2013.01); *B32B 2556/00* (2013.01); *Y10T 428/31504* (2015.04); *Y10T 428/31663* (2015.04)

(58) Field of Classification Search
CPC ....... A61F 2/12; B29C 33/56; B29C 45/0001; B29C 45/0055; B29C 45/1615; B29C 73/00
USPC .................... 156/245, 246; 428/447
See application file for complete search history.

(56) References Cited

U.S. PATENT DOCUMENTS

| | | | |
|---|---|---|---|
| 5,022,942 A * | 6/1991 | Yan et al. ........... | 156/219 |
| 2013/0116783 A1 | 5/2013 | Winn et al. | |

FOREIGN PATENT DOCUMENTS

JP 02055002 A * 2/1990

*Primary Examiner* — Philip Tucker
*Assistant Examiner* — Vicki Wu
(74) *Attorney, Agent, or Firm* — John K. Fitzgerald; Rutan & Tucker, LLP (57) ABSTRACT

A method for injection molding thin materials (sub-millimeter) having low green strength could make certain manufacturing processes significantly more efficient yet has heretofore been unavailable. Provided herein is a method that enables injection molding of thin materials by using a mold with contact surfaces having a low surface energy release agent disposed thereon. The low surface energy release agent may be applied as a coating on a conventional mold or the mold itself or just the contact surfaces thereof may be formed of a low surface energy release material. The method finds particular applicability in making special contour patches for medical and cosmetic implants and prosthetics. A preferred approach involves injection molding a thin layer of unvulcanized material on a cold mold, injection molding a thin layer of vulcanized material on a hot mold, transferring the vulcanized layer to the unvulcanized layer on the cold mold, and removing the combined layers.

18 Claims, 9 Drawing Sheets

METHOD FOR FORMING BILAYER PATCHES

CROSS-REFERENCES TO RELATED APPLICATIONS

This application claims priority from U.S. application Ser. No. 13/290,929, filed Nov. 7, 2011 now abandoned incorporated by reference in its entirety.

BACKGROUND

The present invention is generally directed to the manufacture of medical devices. More specifically, the present invention includes a system and method for manufacturing bilayer adhesive patches that are to be bonded to a medical device that is formed in such a manner that patching is required to complete the manufacture of the device.

Current manufacturing processes to make many medical implantable devices involve forming thin silicone elastomer shells by dipping or molding a thin layer of silicone material on a male mandrel. For example, in the manufacture of breast implants, the outer silicone membrane is formed on a male mandrel. The membrane, typically called a "shell," is removed from the mandrel by cutting a small hole in the shell so that the shell can be removed from the male mandrel without deforming or tearing the shell. Through the hole, the surrounding edges of the shell can then be grasped to stretch and peel the remainder of the shell from the male mandrel more easily. After the shell is off of the mandrel the small circle or hole must be patched to close the shell so as to provide full containment integrity to the shell so that it may then be filled with a filling material, such as a silicone gel.

Current processes of making bilayer patches for medical and cosmetic implants and prosthetics are more difficult, costly, and time-consuming than they need to be. Patches for devices such as breast implants formed from silicone usually have a first layer that is vulcanized, which is then applied to a second layer that is unvulcanized.

Vulcanization generally refers to the process of crosslinking the silicone polymer based material to form a dry, non-adhering material with good elastomeric memory. The vulcanized layer is thin, typically less than 0.5 mm and preferably less than 0.2 mm. Forming thin layers with sticky unvulcanized silicone elastomer bases is difficult and typically done by calendering or solvent based knife-coating, with subsequent devolatilization and vulcanization on a sheet of base plastic such as Teflon® (sold by DuPont), polyester or polyethylene.

The unvulcanized portion or layer of the bilayer patch, typically less than 0.5 mm thick, is typically applied to the vulcanized layer by calendering unvulcanized silicone into a thin layer and then applying that layer to the vulcanized layer described above. Calendering refers to the process of forming a uniform thickness thin layer by pressing uncured malleable elastomer systems between rotating cylinders or rollers. It is difficult to peel thin layers off of the rollers used for calendering without tearing or breaking the fragile thin unvulcanized layer. Accordingly, this process often results in a high loss factor. Alternatively, the unvulcanized layer can be applied to the vulcanized layer by a solvent dispersion technique and subsequently devolatilizing the assembly before proceeding with applying the patch to the shell to close the opening cut into the shell to remove shell from the mandrel. After the vulcanized and unvulcanized layers are joined, they are typically supported on a thin plastic sheet.

Regardless of how the vulcanized silicone layer and unvulcanized silicone layer used to form the patch are combined, once combined both sides are typically covered with a thin layer of a thermoplastic polymer such as polyethylene. The polyethylene covered bilayer sandwich is then cut into the desired size and shape for the patch.

Consistent with current modern manufacturing procedures, the patches are then transferred to another work area in which an assembler manually peels off the polyethylene coating and applies the patch to the shell by placing in into the shell, vulcanized side away from the hole and unvulcanized side facing the hole. Vulcanization and bonding are typically achieved by applying heat and pressure to the assembly.

Another technique that has been investigated for the manufacture of thin patches is the use of injection molding to form the patch. Injection molding of silicone elastomers and plastics is common practice and a well-developed art, though it may also be used for other materials. A wide variety of products are manufactured using injection molding, which vary greatly in their size, shape, complexity, and application.

"Green strength," a measure of tack, deformability, elastic memory and malleability of the unvulcanized silicone elastomer base is a relevant limiting factor to injection molding. Moderate green strength silicone materials typically used in forming silicone elastomer shells do not easily lend themselves to typical mixing systems such as two roll milling (calendering) or pumpable paste static mixer systems.

Green strength can be a good indication of processing behavior and a moderate to high green strength is desirable in processing operations in which it is important to maintain the integrity of a shape piece of material, particularly for the unvulcanized layer.

Thick preforms of high green strength unvulcanized silicone, typically formed by continuous extrusion and chopping, are commonly used in industrial processes. However, injection molding of thin preforms having moderate green strength and tack is not known to have been done before commercially for this application on account of the adhesion between a thin preform of unvulcanized silicone and common mold materials (e.g. aluminum or steel) being too strong to provide a reliable release that preserves the integrity of the thin preform upon removal from the mold. Injection molding of thin preforms is not commercially practical when losses due to the preforms being damaged, deformed, or partially stuck to the mold are too costly.

There is a need for an improved method for forming thin bilayer silicone patches that is less expensive, less labor and time intensive, and that reduces the loss factor of material waste. For example, the traditional process of removing the polyethylene coating is tedious and transporting the patches from one work station to the next for processing creates delays, inefficiencies, and increased costs for labor and facilities. It would be desirable to provide an improved method for forming implant and prosthetic patches in which the patch assembler is able to mold the patches on demand at a single work station. It would be especially desirable to provide a method for injection molding of thin preforms that preserves the integrity of the preforms upon removal from the mold. The present invention satisfies these and other needs.

SUMMARY OF THE INVENTION

In its most general aspect, the present invention provides a process for molding patches for medical and cosmetic implants and prosthetics more efficiently with less material and economic waste. The method provides several improvements over current techniques used in the art of manufacturing patches. For example, the method avoids problems inherent in calendering very thin materials as are required to form the patches.

In a more specific aspect, the present invention provides a way to injection mold unvulcanized and mating vulcanized preforms of very thin materials of low green strength while preserving their integrity upon removal from the mold. According to one aspect of the present invention, this is accomplished by first spraying a mold, including a conventional mold, with a low surface energy release agent that coats the mold and facilitates removal of the preform from it. According to another aspect of the present invention, this is accomplished by using molds in which the portions of the mold that make contact with the preform are formed of different materials than are conventionally used, for example, low surface energy plastics rather than aluminum or steel. Non-contact portions of the mold may or may not still be formed of conventional materials including aluminum or steel.

In another aspect, the present invention provides a process for combining the layers that makeup a patch, specifically the unvulcanized layer and the vulcanized layer. Such a bilayer assembly may be used as formed or subsequently cut into a desired patch shape. In one aspect, patches are molded on demand at a single work station, eliminating the steps of combination through calendering or rolling squeegee technique, coating, and peeling.

Another aspect of the present invention provides a process through which the vulcanized layer may be transferred directly to the unvulcanized layer while the unvulcanized layer remains on a cold mold. The combined layers are together peeled off the cold mold.

In still another aspect, the present invention provides a method of forming a patch that includes: forming a layer of an unvulcanized material to a cold mold having contact surfaces comprising a low surface energy release agent; applying a second layer of a vulcanized material over the first layer of the cold molded unvulcanized material while cold molded layer is still on the cold injection mold; allowing the second vulcanized layer to attach to the unvulcanized layer; removing the combined vulcanized and unvulcanized layers from the cold injection mold; and cutting the bilayer combination into a desired shape for a patch.

According to one aspect, the combination of the unvulcanized layer attached to the vulcanized layer is less than 0.5 millimeter thick. In another aspect, the unvulcanized layer is less than 0.5 millimeter thick. In still another aspect, the unvulcanized material has a low green strength.

In still a further aspect, the vulcanized layer is formed by calendering and subsequent crosslinking of the polymer material. According to one aspect, the vulcanized layer is formed by injection molding on a hot injection mold having contact surfaces comprising a low surface energy release agent. According to still another aspect, the vulcanized layer is less than 0.5 millimeter thick.

In still another aspect, the contact surfaces comprising the low surface energy release agent are formed by applying a coating of the low surface energy release agent to the contact surfaces of the hot or cold injection mold. According to another aspect, the contact surfaces of the hot or cold injection mold are made of a material that has a low surface energy.

In a further aspect, the low surface energy release agent is a fluorinated polymer. In yet a further aspect, the low surface energy release agent is polyvinylidene fluoride. In another aspect, the low surface energy release agent is polyvinylidene chloride, and in yet another aspect, the low surface energy release agent is poly(p-xylylene). In still another further aspect, the low surface energy release agent is polytetrafluoroethylene, and in yet another aspect, the low surface energy release agent is a plastic.

In another aspect, the method further includes forming a label or bar code on at least one layer that will be visible on the patch. According to one aspect, the label is an identifying label that may be used for tracking a manufacturing history of an implant or prosthesis to which the patch is applied.

In still another aspect, the method further includes forming an aperture in the patch through which a filler material may be supplied to an implant or prosthesis upon which the patch is applied, the aperture configured to be sealed after an implant or prosthesis is filled.

In yet another aspect, the method includes forming special contours on the patch designed to minimize the transition between the edge of the hole in the shell and the edge of the patch.

In another aspect, the method includes forming special contours on or in the patch to minimize the flow under pressure between the outer edge of the patch and the edge of the hole in the shell.

In still another aspect, the invention includes a method of forming a patch, comprising: injection molding a vulcanized polymer layer using a first mold plate; injection molding a unvulcanized polymer layer using a second mold plate; removing the vulcanized polymer layer from the first mold plate; disposing the vulcanized polymer layer onto the unvulcanized layer while the unvulcanized layer is still on the second mold plate. compressing the vulcanized polymer layer and the unvulcanized polymer layer until the vulcanized polymer layer adheres to the unvulcanized layer to form a patch; and removing the patch from the second mold plate.

In an alternative aspect, the second mold plate has a contact surface upon which the unvulcanized polymer layer is formed that is formed from a low surface energy material. In another aspect, the low surface energy material is selected from the group consisting of polytetrafluoroethylene, and polyvinylidene fluoride.

In yet another aspect, the second mold plate has a contact surface upon which the unvulcanized polymer layer is formed, the contact surface formed from a release agent bonded to the second mold plate. In still another aspect, the release agent is a low surface energy material. In another aspect, the release agent is a fluorinated polymer. In yet another aspect, the release agent is selected from the group consisting of polyvinylidene fluoride, polyvinylidene chloride, and poly(p-xylylene).

In another aspect, the invention may include applying a release coating to a contact surface of the second mold plate upon which the unvulcanized polymer layer is formed. I an alternative aspect, the release coating is a fluorinated polymer. In still another alternative aspect, the release agent is selected from the group consisting of polyvinylidene fluoride, polyvinylidene chloride, and poly(p-xylylene).

In still another aspect, the invention includes forming a layered patch, comprising: injection molding an unvulcanized layer by molding the unvulcanized layer against a first mold having a low surface energy contact surface; forming a vulcanized layer; applying the vulcanized layer over the unvulcanized layer while the unvulcanized layer is still on the first mold; adhering the vulcanized layer to the unvulcanized layer; removing the adhered vulcanized and unvulcanized layers from the first mold; and cutting the adhered vulcanized and unvulcanized layers into a desired shape for a patch.

In another aspect, the forming vulcanized layer includes injection molding; in an alternative aspect forming the vulcanized layer includes calendering; and in still another aspect, forming the vulcanized layer includes hot injections molding to cure and vulcanize the vulcanized layer.

In yet another aspect, injection molding the unvulcanized layer includes using a cold injection molding process. Alternatively, injection molding the unvulcanized layer includes using a cold mold.

In still another aspect, the low energy surface of the mold is created by coating a surface of the mold with low surface energy material. In an alternative aspect, the low energy surface of the mold is created by bonding a release agent to a surface of the mold. In yet another aspect, the mold having a low energy surface is formed from a material having a low surface energy. In one alternative aspect, the low surface energy material is a fluorinated polymer; in another alternative aspect, the low surface energy material is polyvinylidene fluoride; in another alternative aspect, the low surface energy material may be polyvinylidene chloride, poly(p-xylylene), or polytetrafluoroethylene.

In yet another aspect, forming the vulcanized layer includes solvent casting.

In another aspect, injection molding the unvulcanized layer includes molding a contour into the unvulcanized layer. In still another aspect, injection molding the unvulcanized layer includes molding forming means for providing an insertion point in the patch for filling an implantable silicone breast prosthesis with fluid. In an alternative aspect, the fluid is a silicone gel.

In yet one more aspect, the present invention includes an implantable silicone breast prosthesis manufactured using any of the aspects of the invention set forth above. Alternatively, the present includes a patch formed using any of the aspects of the invention described previously.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

In one of its various embodiments, the present invention provides a process of making patches for medical and cosmetic implants and prosthetics in which the patches can be made on demand and applied to the implant, prosthetic, or a shell thereof or precursor thereto at a single workstation. This process reduces material losses from calendering and saves labor and facilities costs due to the elimination of coating (before cutting) and peeling the coating off (after cutting) steps and the ability to concentrate the process at a single workstation.

Another aspect of the invention involves coating the mold material used to injection mold the layers that form the patch with a low surface energy release agent in order to facilitate removal of the layers given the low green strength and propensity for adhesion of thin preform materials. The low surface energy release agent may be, for example, a fluorinated polymer, polyvinylidene fluoride, polyvinylidene chloride, poly(p-xylylene), and like compositions.

Alternatively or additionally to coating the mold material with a low surface energy release agent, the portions of the mold that make contact with the preform material that forms the patch layer ("contact portions"), may themselves be made of a selected material to facilitate removal. For example, contact portions of the mold may be made of a low surface energy plastic, polytetrafluoroethylene (PTFE), polyvinylidene fluoride, or like materials. Or, the entire mold may be made of one of these materials mentioned above to facilitate removal of thin preforms with low green strength and high adhesion.

Prior to bringing the layers together the vulcanized layer is preferably formed by a hot injection mold while the unvulcanized layer is preferably formed by a cold injection mold. The vulcanized layer is then peeled off the hot injection mold and transferred to and applied over the unvulcanized layer on the cold injection mold. Once the layers are properly in contact with each other the combination can be pulled from the cold injection mold.

The preferred patch is typically made from the combination of a layer of 0.2 mm thick vulcanized silicone with a layer of 0.2 mm thick unvulcanized silicone. One desirable application for the thin preform injection molding process is to make patches for breast implants. For this application, the vulcanized layer is made of a special silicone that is so sticky it must be solvent cast into thin films or injection molded from solvent free paste.

The vulcanized layer may be transferred to the unvulcanized while it is still hot from the curing process in order to promote adhesion. The weight of the hotter vulcanized layer over the unvulcanized layer may be enough to promote bonding and adhesion between the two layers that will securely combine the layers with time. However, light pressure may also be applied to encourage the vulcanized and the unvulcanized layers to come together to form a singular combination layer. Light pressure may be applied, for example, by blowing air or an inert gas on the layers as the vulcanized layer cools over the unvulcanized layer. The layers may be allowed to rest together for up to, for example, but not limited to, twenty (20) minutes to mate until they are securely attached to each other.

The patches and methods of producing patches described herein are suited for patching holes in a shell that is a precursor to an implant. Typically, a hole is intentionally created in a shell in order to more easily remove it from a mandrel on which it is formed. After a shell is patched, filler material may be injected into the implant shell through the patch to form a completed implant ready for implantation. Or, in the case of some implants and tissue expanders, the device may be inserted without filler material or with less than the final amount of filler material which can be added after implantation through a port in the patch. Common filler materials for breast implants, for example, include silicone gels and saline solutions.

Optionally, a label may be formed on the patch during the molding process. The label may be two or three dimensional. The label may be formed by painting onto a layer used to form the patch or it may be embossed on a layer through surface topography provided on the injection mold or mandrel used to form the patch. The label may be an identifying label that provides tracking information as to the manufacturing history of the implant that may be useful in recognizing, reporting, and ameliorating any issues that may arise due to particular implants. If each patch receives a unique label, the label may be formed by a unique three-dimensional identifier (e.g. a sticker, a magnet, etc.) that is applied to an injection mold or mandrel before the patch is formed thereon such that a three-dimensional design will be imprinted into the patch.

To provide appropriate background to the process of patching described herein, the process of fabricating implant shells is outlined with a focus on shells for breast implants or mammary prostheses. Breast implant shells are generally formed on mushroom-shaped mandrels by applying a liquid dispersion of a silicone elastomer to the mushroom-head structure of the mandrel. The silicone dispersion used to form the shell may be applied by any one of several methods including dipping or dip-molding, rotational molding (see, for example, U.S. Pat. No. 6,602,452, incorporated by reference herein in its entirety), spraying, brushing, painting, and the like.

In many situations it is preferable that the mandrel have a textured or porous surface that is transferable to the surface texture of the shell. Implants having surface texture, variable surface topography, or micropillars have been shown to provide several post-implantation advantages inside a patient's body that reduce post-surgical complications and improve a body's acceptance and tolerance of the implant. See, for example, European Patent No. 0416846 and European Patent No. 0710468, both of which are incorporated by reference herein in their entirety.

Exemplary materials for mandrels include a hard resinous polymeric material such as epoxy or polyester (e.g. polyethylene terephthalate), polyvinylidene fluoride, polyacetal (homo or copolymer), polytetrafluoroethylene, perfluoroethylene or other fluoropolymers. Mandrels may also be formed of inert metals such as nickel or stainless steel, or ceramics.

In manufacturing the shell, the mandrel may be successively coated with several layers of the shell material dispersion with devolatilization to ensure silicone is deposited in the proper thickness. After the desired number of layers of liquid shell material are applied to the mandrel, the mandrel coated with shell material is cured at elevated temperatures such as, for example, 90 to 250 degrees centigrade, depending on the particular polymers in the dispersion, for 0.5 to 6 hours. The cured elastomer shell is then allowed to cool on the mandrel before a hole is created in the shell to peel it off the mandrel.

Figure 1:
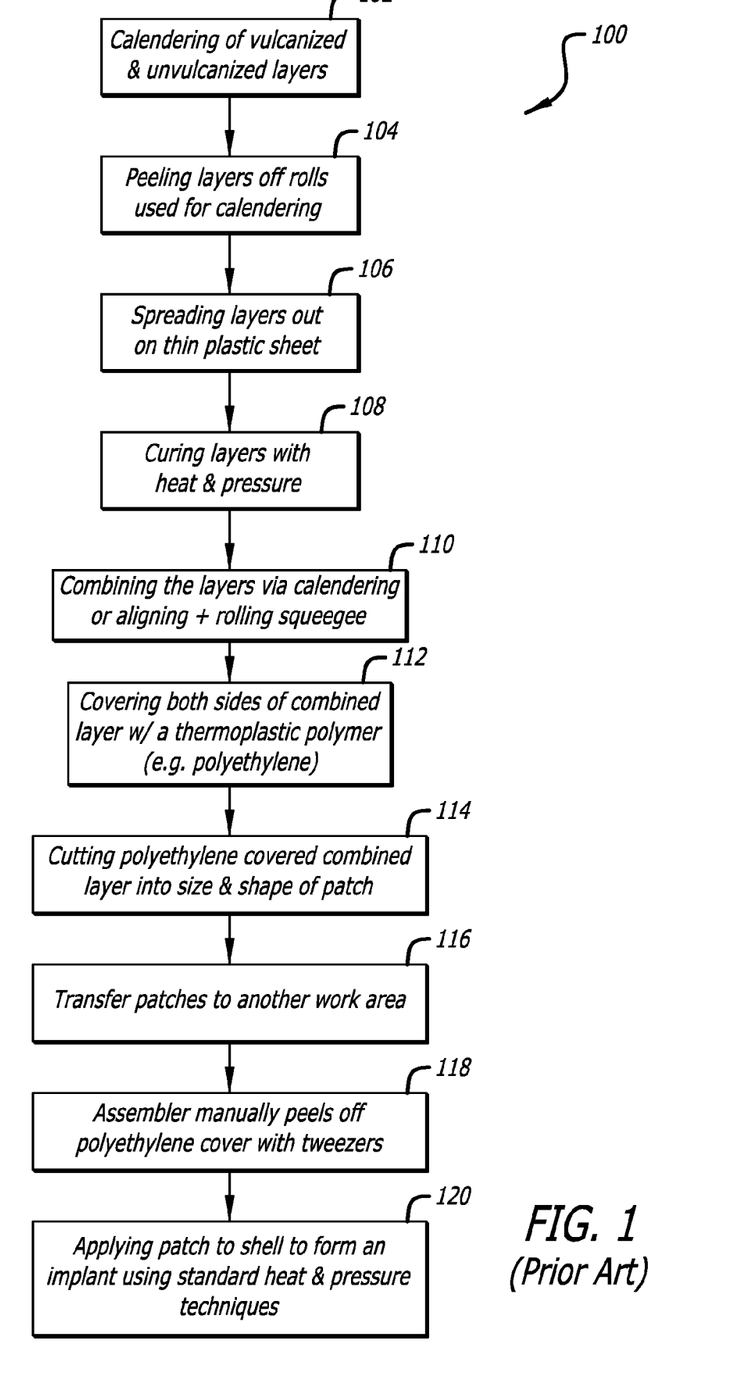
FIG. 1 is a flow chart illustrating a prior art process of making patches.

As shown in FIG. 1, in accordance with the traditional process 100 for forming patches for implant shells several steps are required which take place across several separate works stations. The process typically begins at Box 102 with the calendering of vulcanized and unvulcanized layers used to form the patches. The thin calendered layers are manually peeled off of the rollers used for calendering at Box 104. It is not uncommon for layers to be torn, damaged, or partially destroyed during this peeling process and accordingly the loss rate is generally higher than desirable and contributes to the inefficiency of the traditional process.

Next, the calendered layers are spread onto a thin plastic sheet at Box 106. The layers are then cured with heat under pressure in Box 108.

The separately calendered and cured vulcanized and unvulcanized layers are then combined together through further calendering or by aligning the sheets which are then combined using a rolling squeegee technique in Box 110. One or both sides of the combined layer sandwich are then coated with a thermoplastic polymer at Box 112. The thermoplastic polymer applied to cover the combined layer sandwich may be, for example, polyethylene. However, other thermoplastic polymers other than polyethylene may also be used as a coating on the combined layer sandwich.

Subsequently, the thermoplastic polymer covered sandwich of combined layers (one layer vulcanized, another layer unvulcanized) is cut into the size and shape desired for an implant shell patch at Box 114. The patches may then be transferred to another work station in Box 116. At that work station, an assembler manually peels the thermoplastic polymer cover off of the patch with tweezers in Box 118. Finally, with the thermoplastic cover removed, the patch is applied to a shell to form an implant using standard heat and pressure techniques at Box 120.

Figure 2:
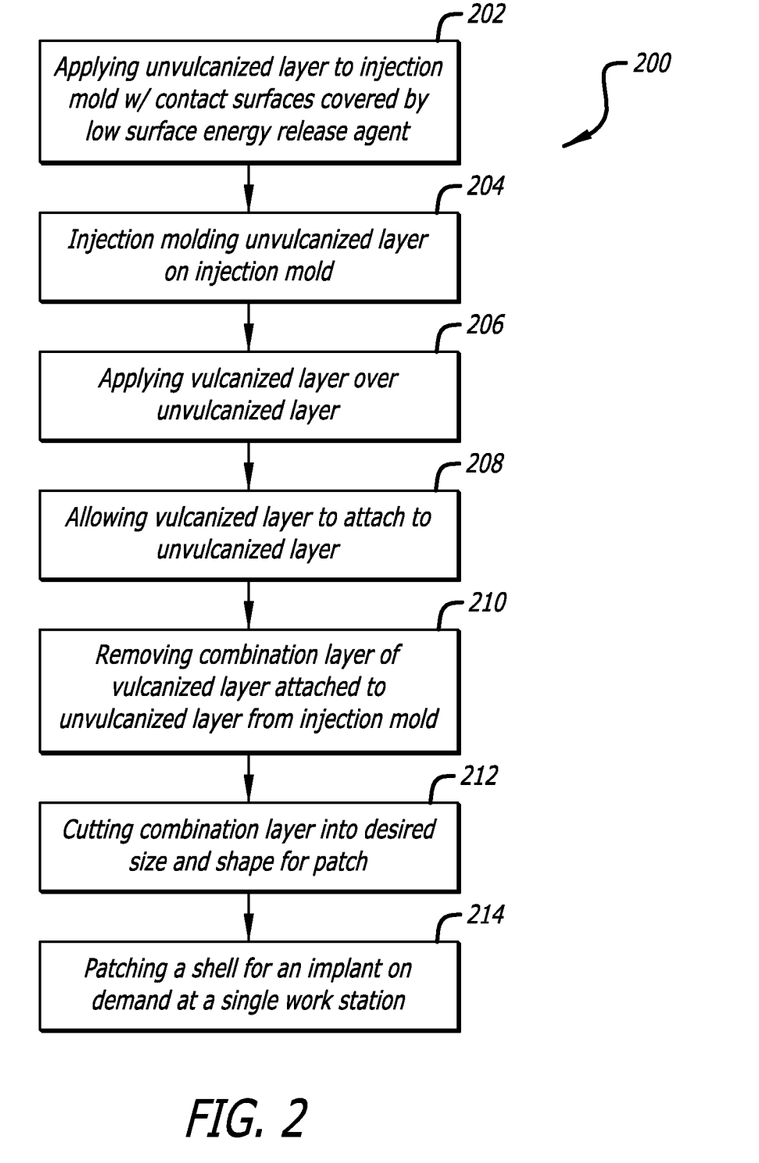
FIG. 2 is a flow chart illustrating a process of making patches in accordance with an embodiment of the present invention.

As shown in FIG. 2, broadly and in general terms, in accordance with the process 200 according to one of several embodiments of the present invention, an unvulcanized materials is injected into a mold assembly having a contact surface covered with a low surface energy release agent at Box 202. The unvulcanized layer is then injection molded on the injection mold at Box 204. The injection mold used may be a cold injection mold or a hot injection mold. Typically, the mold assembly used for injection molding the unvulcanized layer is a cold injection mold.

At Box 206, a separate vulcanized layer is then applied over the unvulcanized layer on the mold assembly. A period of time should be allowed, and possibly also some physical pressure applied, to allow the vulcanized layer to securely attach to the unvulcanized layer on the mold in 208.

Once the two layers are firmly adhered to each other upon the mold assembly used to injection mold the bottom unvulcanized layer, the combination of layers is removed from the injection mold at Box 210.

The combination of layers is then cut into the desired size and shape for patches at Box 212. The patches are then applied to a shell on demand in Box 214. Each of the above steps may be performed at a single work station.

Figure 3:
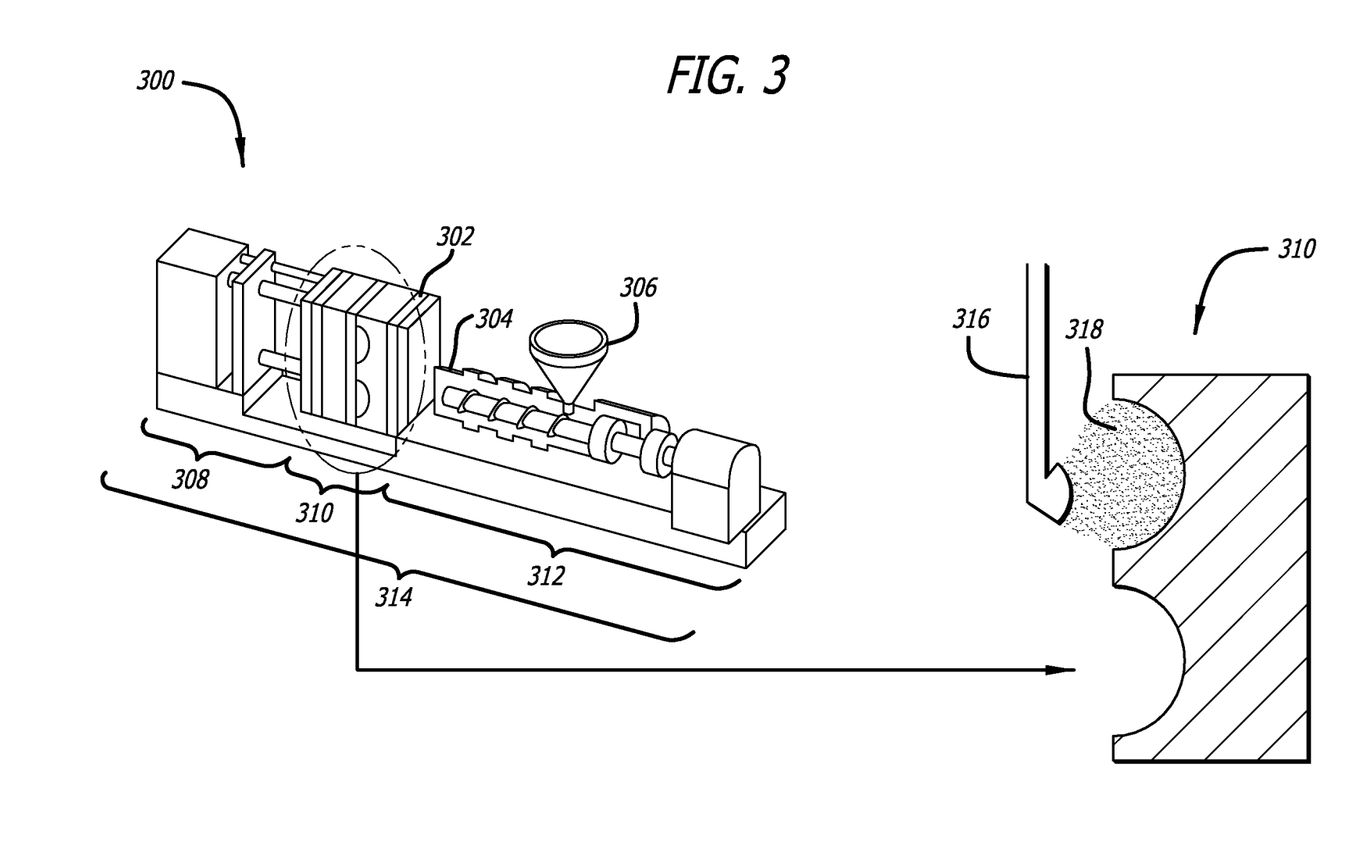
FIG. 3 shows a conventional injection mold, hot or cold, being coated with a low surface energy release agent in accordance with an embodiment of the present invention.
Figure 4:
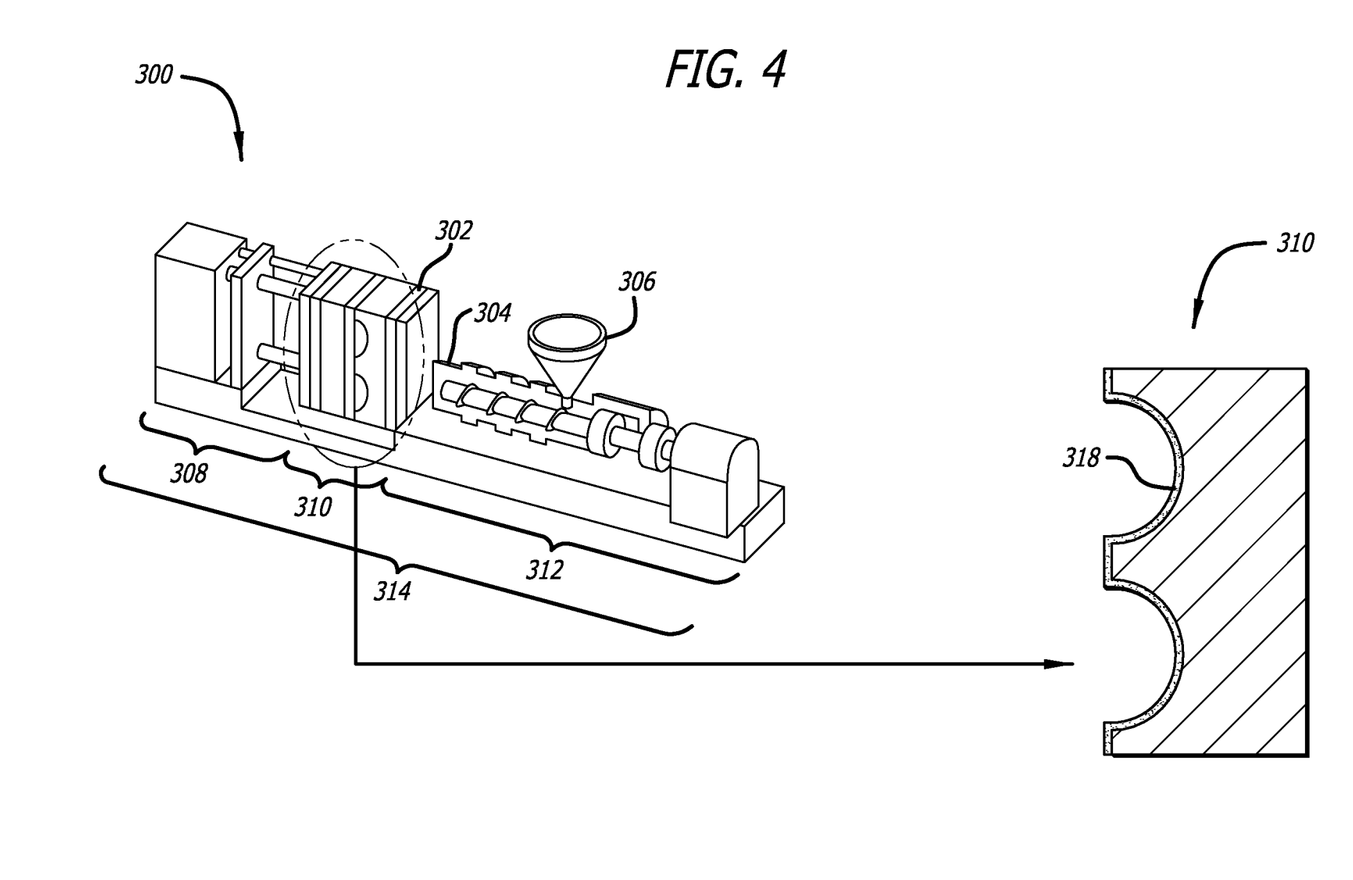
FIG. 4 shows an injection mold, hot or cold, having contact portions made of a low surface energy release material in accordance with an embodiment of the present invention.

As shown in FIG. 3, in accordance with an embodiment 300 of the present invention, a conventional injection mold, hot or cold, is coated with a low surface energy release agent. The conventional injection mold includes molded part 302, molten plastic 304, raw plastic 306, clamping unit 308, mold assembly 310, injection unit 312, and injection molding machine 314. The enlarged view of the mold assembly 310 illustrates using a sprayer 316 to apply a coating 318 of a low surface energy release agent on the surface of the mold assembly that will make contact with the molten plastic 304 to form a molded part 302. As shown in FIG. 4, the coating 318 of a low surface energy release agent has been applied upon all contact surfaces of the mold assembly 310.

Figure 5:
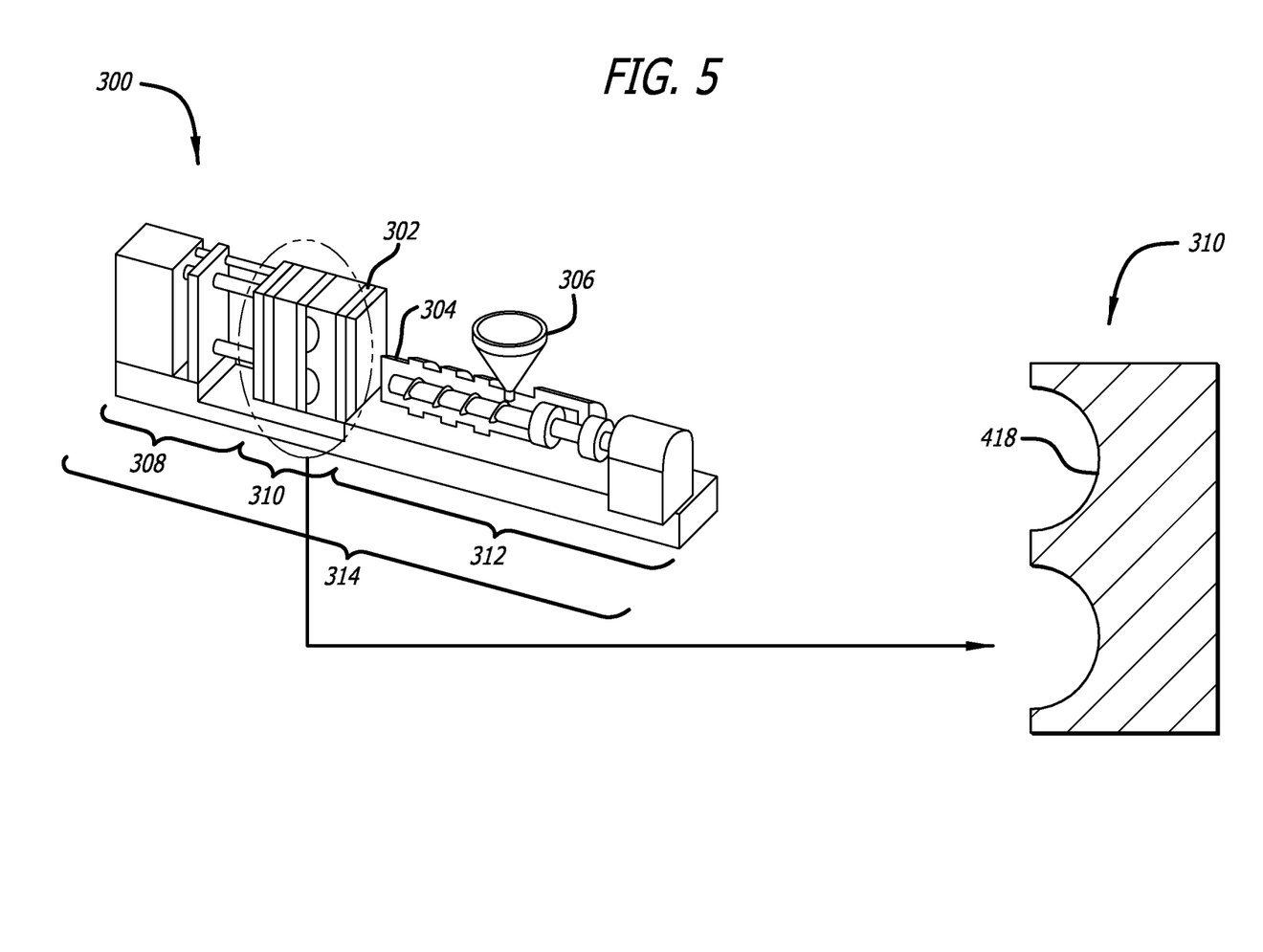
FIG. 5 shows an injection mold, hot or cold, formed of a low surface energy release material in accordance with an embodiment of the present invention.

As shown in FIG. 5, in accordance with another embodiment of the present invention, a conventional injection mold is modified such that the mold assembly 310 is formed entirely of a material 418 that is a low surface energy release agent. Alternatively, the mold assembly 310 may be formed such that all contact surfaces include a material 418 that is a low surface energy release agent. In either of these embodiments, a coating is not needed because the mold assembly itself, or at least the contact surfaces thereof, are already formed of a low surface energy release material.

Figure 6:
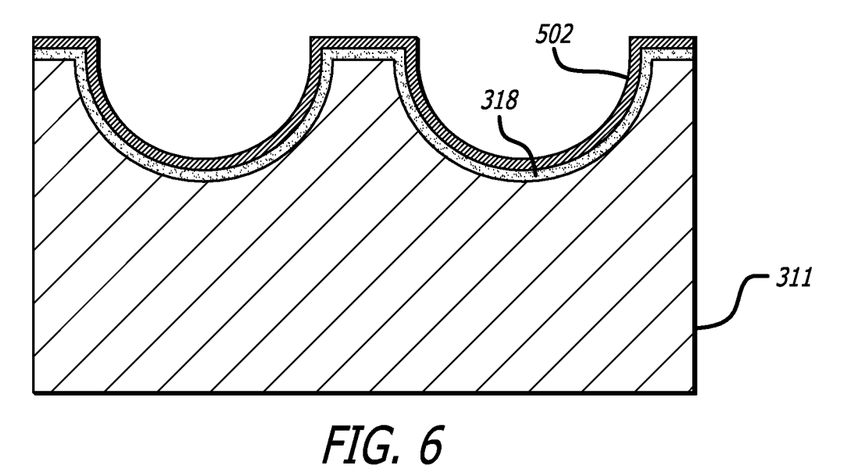
FIG. 6 is a cross-sectional view showing a vulcanized layer being applied to a hot injection mold having a low surface energy release material between the mold and the vulcanized layer.

As shown in FIG. 6, a heat curable and/or vulcanizable material is injected into a hot injection mold assembly 311 upon which a coating 318 of a low surface energy release agent has already been applied. A vulcanized layer 502 is then formed by curing and vulcanizing the vulcanizable material, such as a silicone elastomer within the hot mold assembly.

Figure 7:
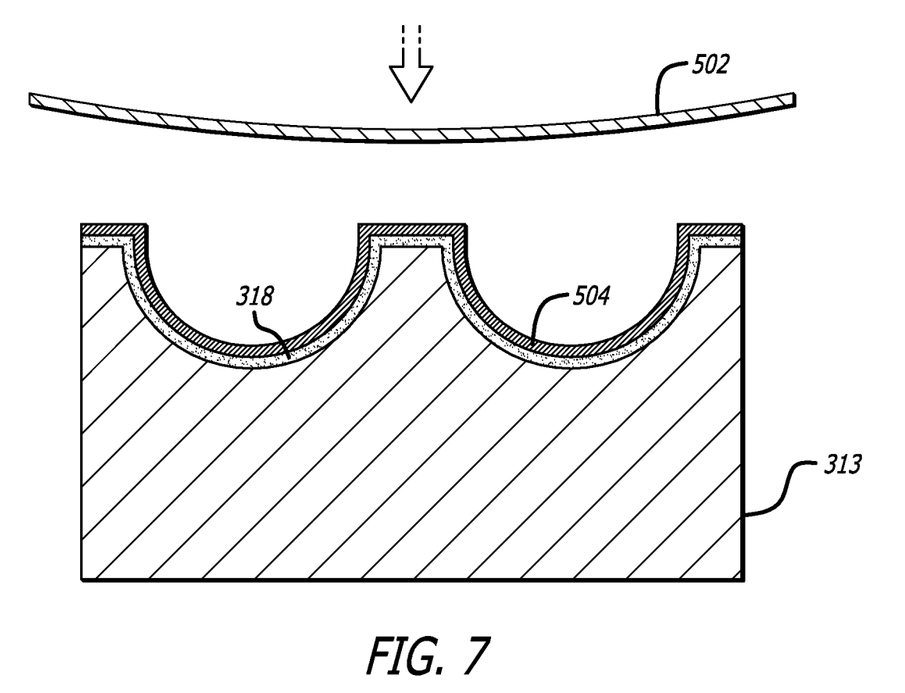
FIG. 7 a cross-sectional view showing the vulcanized layer, after removal from the hot injection mold, being transferred to and applied over an unvulcanized layer on a cold injection mold, the cold mold also having a low surface energy release material.
Figure 8:
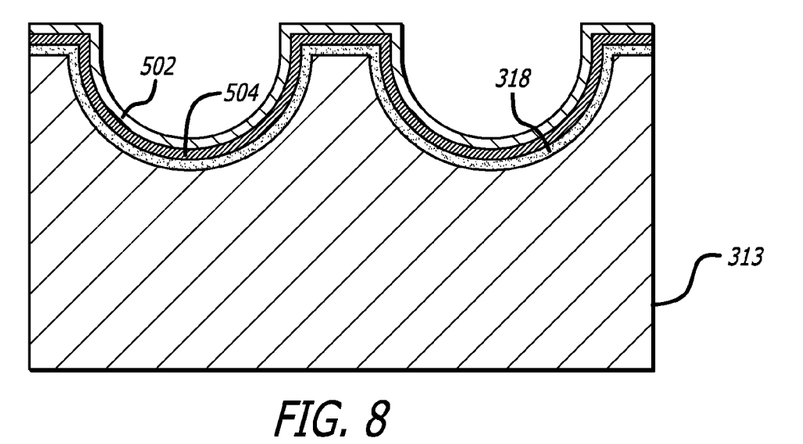
FIG. 8 a cross-sectional view showing the vulcanized layer making contact with the unvulcanized layer on the cold injection mold.

As shown in FIG. 7 and FIG. 8, the vulcanized layer 502 from the hot injection mold assembly 311 is transferred to a cold injection mold assembly 313, upon which a coating 318 of a low surface energy release agent has been applied, the cold injection mold assembly 313 already having an unvulcanized layer 504 formed thereon over which the vulcanized layer 502 is applied. The unvulcanized layer 504 was formed by injecting a suitable material, such as a silicone elastomer or its precursors, into a cold mold assembly. The mold assembly is then opened up, and the vulcanized layer 502 applied over the unvulcanized layer 504 while the unvulcanized layer 504 remains in the mold assembly. Referring now to FIG. 8, the thin vulcanized layer 502, conforms to the shape of the mold and thus also to the shape of the unvulcanized layer 504. It will be apparent to those skilled in the art that while the process is described with reference to mold plates having a particular shape formed therein, any shape may be molded into the various layers, or the layers may be formed in such a manner that they are essentially flat.

Figure 9:
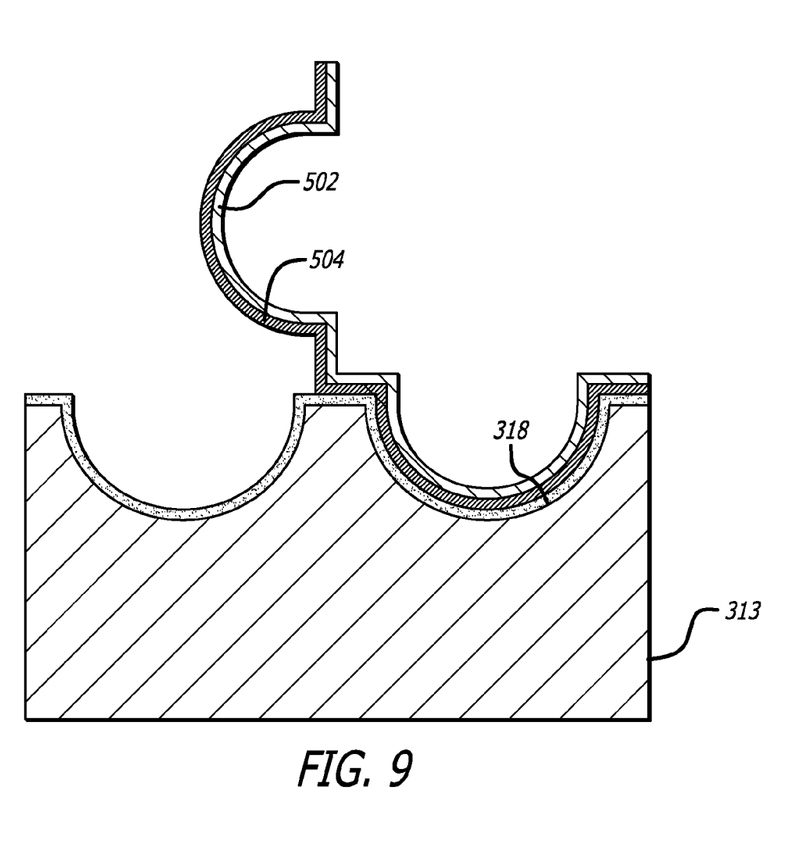
FIG. 9 a cross-sectional view showing the combination of the vulcanized layer and the unvulcanized layer bonded together being pulled off of the cold injection mold having a low surface energy release material.

As shown in FIG. 9, the vulcanized layer 502 adheres to the unvulcanized layer 504 on the cold injection mold 313, mating the layers to each other. The bilayer assembly comprising vulcanized layer 502 and unvulcanized layer 503 may then be peeled off of the mold as illustrated, maintaining the integrity of the bilayer patch assembly.

Figure 10:
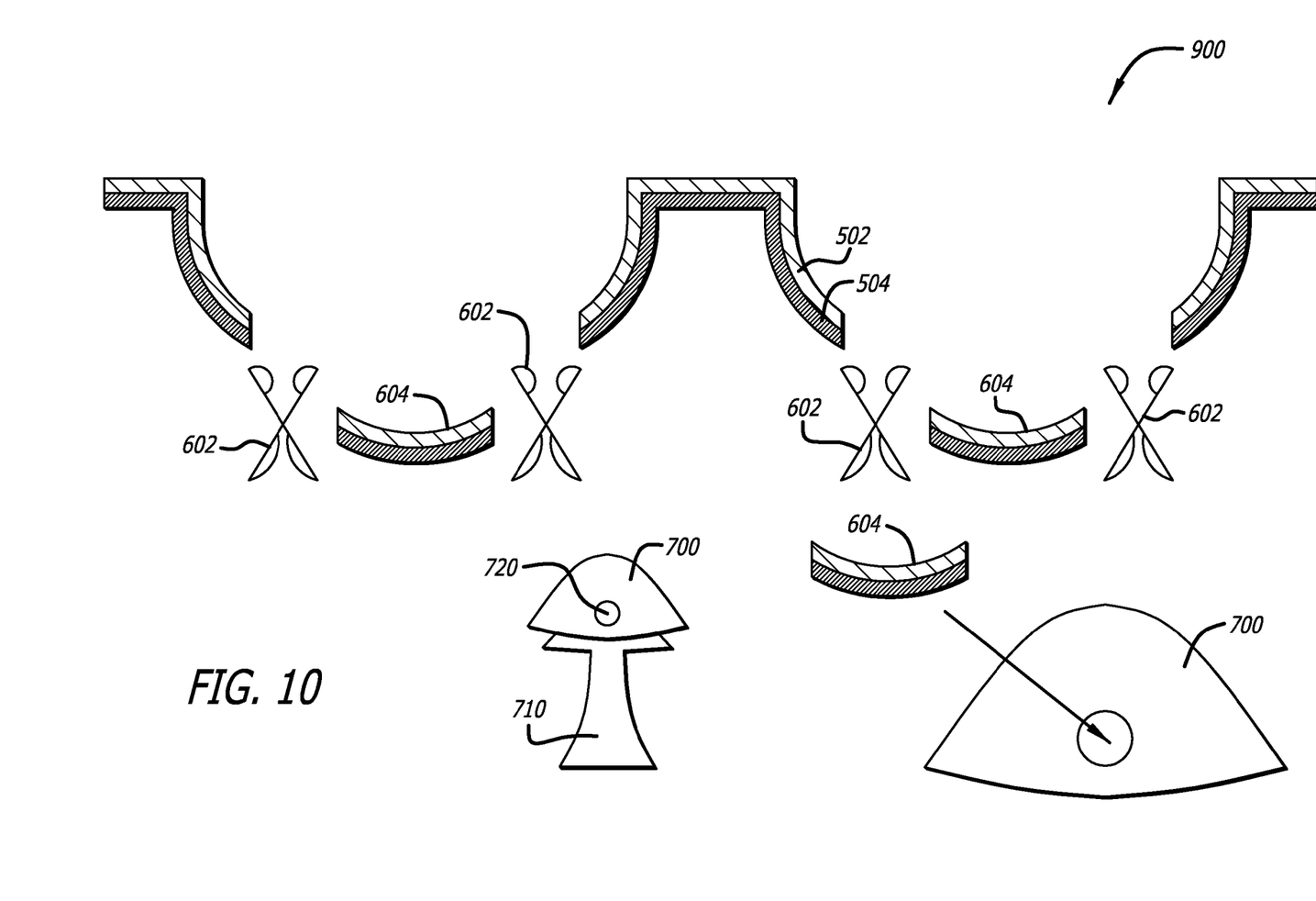
FIG. 10 is a graphical representation of one embodiment of a process used to cut the combination of the vulcanized layer and the unvulcanized layer into the desired shape for a patch and application of the patch to the implant or prosthetic shell at a single work station.

Referring now to FIG. 10, upon peeling the combined layers off of the mold assembly, the adhered layers 602 can be used as formed or cut into the desired shape and size for the implant shell patches. A cutout section 604, or patch, of the combined layers is then transferred over to an implant shell 700 on a mandrel 710 and applied over a hole 720 in the shell. This entire process, from cutting the adhered layers into sections to patching the hole in the implant shell on a mandrel, can occur at a single work station 900.

Figure 11:
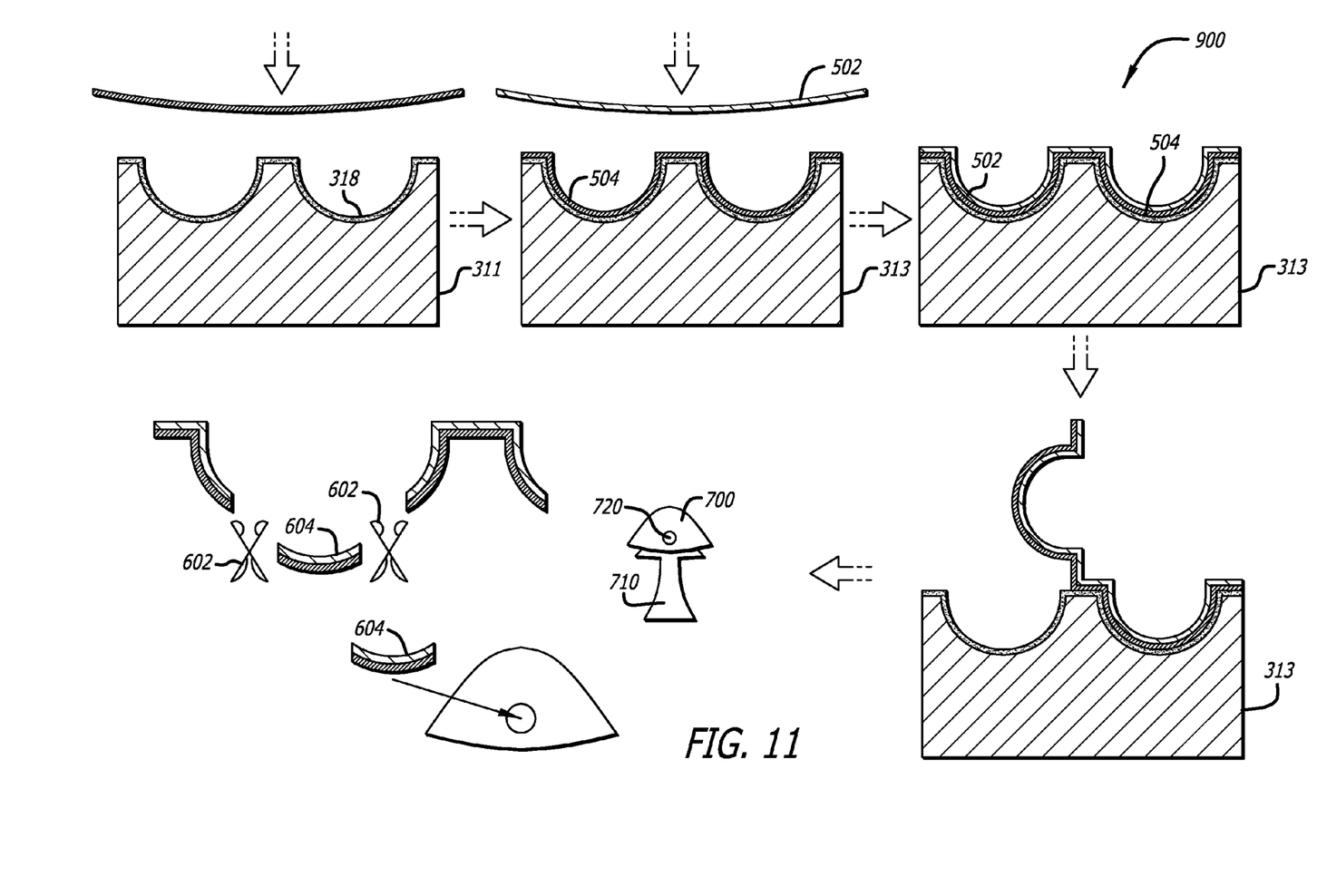
FIG. 11 is a graphical flow diagram illustrating the steps of forming the layers through injection molding, combining the layers, peeling the layers off the mold, cutting the combined layers into a patch, and applying the patch to the implant all being performed at a single work station.

FIG. 11 illustrates how all steps of the process from forming the vulcanized layer on a hot injection mold assembly as in FIG. 6, to transferring the vulcanized layer to an unvulcanized layer on a cold injection mold assembly as in FIG. 7, to applying the vulcanized layer over the unvulcanized layer already on the cold injection mold as in FIG. 8, to peeling the adhered layers off the cold injection mold assembly as in FIG. 9, to cutting the adhered layers into patch sections and applying over a hole in an implant shell on a mandrel as in FIG. 10, may be performed at a single work station 900.

According to one embodiment, the injection molding process used requires the use of an injection molding machine, raw material, and a mold. The process outline that follows assumes fabrication of a plastic part as a representative example but is not intended as being limited to fabrication of plastic parts.

First, if the contact surfaces of the injection mold are not composed of a low surface energy release material or the mold is not formed of a low surface energy release material, the contact surfaces of the mold should be coated with a low surface energy release agent. Any known manner of coating the mold surfaces may be used to apply the low surface energy release agent coating, including painting on the coating, spraying on the coating, dipping the mold into a solution of coating, condensing vapors of the coating material onto the mold, and the like. Alternatively, the release surface may be highly polished to facilitate release of the material from the molds.

Next, the mixed unvulcanized silicone elastomer components are loaded into the injection molding machine and then injected into the preheated mold, where the silicone elastomer components are cured and vulcanized into the final part. The process cycle for injection molding is very short, typically between 2 seconds and 2 minutes.

The main stages of the injection molding process are well known in the art and include clamping, injection, and ejection. Clamping refers to the step of securely closing and locking the two halves of the mold by the clamping unit prior to injection of any material into the mold. In the injection stage, the material used to form the molded object, which may be a viscous fluid like material such as an uncured silicone, is fed into the injection molding machine, and advanced towards the mold by the injection unit. The molding material is generally is forced into the cavity of the mold under high pressure to ensure proper filling of the mold cavity.

The mold plates in the injection molding machine may be heated or cooled, dependent upon the material being used and the desired properties of the finished molded article. In one embodiment of the present invention, the vulcanized layer is formed by heating the mold plate to cure and vulcanize the silicone material injected into the mold. The unvulcanized layer, in contrast, is injected into a cold plate so that the silicone may cure without vulcanizing.

In the ejection stage, the molded part or article, is often ejected from the mold. This ejection process is not typically used in the various embodiments of the present invention. Rather, the thin vulcanized and unvulcanized silicone layers are carefully peeled from the mold cavity.

As described previously, use of a low surface energy release material for construction of the mold plates, or which is applied to a standard metal mold plate, to promote release of the molded article is particularly advantageous when forming the thin layers of vulcanized and unvulcanized silicone of the present invention. Use of such a release agent allows removal of the thin layers of unvulcanized silicone having low green sheet from the molds while reducing the incidence of damage to the layers during the removal step.

Further, the use of injection molding apparatus and method that provides for easy release of the vulcanized and unvulcanized layers allows for the combination of multiple manufacturing steps so that the entire process of manufacturing a patch may be carried out at a single work station by a single operator. Such a process provides for a reduction in product loss due to damage, increased productivity and lower manufacturing costs.

The present invention is not limited to the embodiments described above. Various changes and modifications can, of course, be made, without departing from the scope and spirit of the present invention. Additional advantages and modifications will readily occur to those skilled in the art. Accordingly, various modifications may be made without departing from the spirit or scope of the general inventive concept as defined by the appended claims and their equivalents.

What is claimed is:

1. A method of forming a layered patch, comprising: injection molding an unvulcanized layer by molding the unvulcanized layer against a first mold having a low surface energy contact surface; forming a vulcanized layer; applying the vulcanized layer over the unvulcanized layer while the unvulcanized layer is still on the first mold; adhering the vulcanized layer to the unvulcanized layer; removing the adhered vulcanized and unvulcanized layers from the first mold; and cutting the adhered vulcanized and unvulcanized layers into a desired shape for a patch.

2. The method of claim 1, wherein forming the vulcanized layer includes injection molding.

3. The method of claim 1, wherein forming the vulcanized layer includes calendaring.

4. The method of claim 2, wherein forming the vulcanized layer includes hot injections molding to cure and vulcanize the vulcanized layer.

5. The method of claim 1, wherein injection molding the unvulcanized layer includes using a cold injection molding process.

6. The method of claim 1, wherein injection molding the unvulcanized layer includes using a cold mold.

7. The method of claim 1, wherein the low energy surface of the mold is created by coating a surface of the mold with low surface energy material.

8. The method of claim 1, wherein the low energy surface of the mold is created by bonding a release agent to a surface of the mold.

9. The method of claim 1, wherein the mold having a low energy surface is formed from a material having a low surface energy.

10. The method of claim 7, wherein the low surface energy material is a fluorinated polymer.

11. The method of claim 10, wherein the low surface energy material is polyvinylidene fluoride.

12. The method of claim 10, wherein the low surface energy material is polyvinylidene chloride.

13. The method of claim 10, wherein the low surface energy material is poly(p-xylylene).

14. The method of claim 10, wherein the low surface energy material is polytetrafluoroethylene.

15. The method of claim 1, wherein forming the vulcanized layer includes solvent casting.

16. The method of claim 1, wherein injection molding the unvulcanized layer includes molding a contour into the unvulcanized layer.

17. The method of claim 1, wherein injection molding the unvulcanized layer includes molding forming means for providing an insertion point in the patch for filling an implantable silicone breast prosthesis with fluid.

18. The method of claim 17, wherein the fluid is a silicone gel.

* * * * *